United States Patent [19]

Christenson et al.

[11] 4,100,183

[45] Jul. 11, 1978

[54] PROCESS FOR PREPARING CUPROUS ALUMINUM TETRAHALIDE COMPLEXING AGENTS

[75] Inventors: Christopher P. Christenson, Lake Jackson, Tex.; John W. Faller, Hamden, Conn.; Gary M. McNamee, Lake Jackson, Tex.

[73] Assignee: The Dow Chemical Company, Midland, Mich.

[21] Appl. No.: 793,205

[22] Filed: May 2, 1977

[51] Int. Cl.$^2$ .............................................. C07F 1/08
[52] U.S. Cl. ................................ 260/438.1; 423/463; 423/464; 423/493
[58] Field of Search ................... 260/438.1; 423/493, 423/463, 464

[56] References Cited

U.S. PATENT DOCUMENTS

| 3,143,542 | 8/1964 | Ziegler et al. | 260/448 A |
|---|---|---|---|
| 3,440,296 | 4/1969 | Walker | 423/463 X |
| 3,592,865 | 7/1971 | Long et al. | 260/677 A |
| 3,647,843 | 3/1972 | Walker et al. | 260/438.1 |
| 3,651,159 | 3/1972 | Long et al. | 260/667 |
| 3,754,047 | 8/1973 | Long et al. | 260/677 R |
| 3,755,487 | 8/1973 | Jahnig et al. | 260/677 A |
| 3,758,606 | 9/1973 | Horowitz et al. | 260/677 A |
| 3,767,725 | 10/1973 | Walker et al. | 260/679 A |
| 3,845,188 | 10/1974 | Walker | 423/493 X |
| 3,857,869 | 12/1974 | Turnbo | 260/438.1 |

OTHER PUBLICATIONS

Chemical Abstracts, 82, 25290a (1975).
Chemical Abstracts, 77, 113556u (1972).

*Primary Examiner*—Helen M. S. Sneed
*Attorney, Agent, or Firm*—James G. Carter

[57] ABSTRACT

Cuprous aluminum tetrahalide complexing agents are prepared from cuprous halide such as cuprous chloride contaminated with cupric halide by a method which reduces the cupric ion to the cuprous ion by treating the contaminated cuprous halide with an organo metal compound, such as metal alkyls, metal alkyl halide or metal alkoxides such as diethyl aluminum chloride prior to preparation of the complexing agent by reacting the cuprous halide with an aluminum trihalide such as aluminum trichloride. The pretreatment to remove the cupric ions reduces the amount of aromatic tars formed in processes employing the complexing agents.

7 Claims, No Drawings

PROCESS FOR PREPARING CUPROUS ALUMINUM TETRAHALIDE COMPLEXING AGENTS

SUMMARY OF THE INVENTION

The present invention is directed to a process for the preparation of cuprous aluminum tetrahalide complexing agents from cuprous halides contaminated with cupric halide by reducing the cupric ions with an organo metal compound.

BACKGROUND OF THE INVENTION

Various bimetallic salts and derivatives thereof have been employed in the preparation of scavengers or complexing agents for various ligands such as olefins, aromatics, carbon monoxide and the like as disclosed in U.S. Pat. Nos. 3,592,865; 3,647,843; 3,651,159; 3,754,047 and 3,755,487. One of the more popular bimetallic salts is cuprous aluminum tetrahalide ($CuAlCl_4$) generally prepared by reacting a cuprous halide with an aluminum trihalide in a suitable solvent. Such commercially available cuprous halides generally contain some quantities of cupric halide which is believed to promote the formation of aromatic tars when the resultant cuprous aluminum tetrahalide is employed as the complexing agent. The present invention is believed to prevent or lessen the tendency for such complexing agents to form tars during adsorption processes employing such complexing agents.

DETAILED DESCRIPTION OF THE INVENTION

The present invention is directed to an improved process for preparing cuprous aluminum halide complexing agents which are essentially free of cupric compounds which process comprises reacting a cuprous halide with an aluminum halide in the presence of a suitable solvent, the improvement being contacting the cuprous halide containing cupric halide, prior to reaction with the aluminum halide, with an organo metal, organo metal halide or organo metal alkoxide wherein said metal is selected from a member of Groups IA, IIA, IIB and IIIA of the Periodic Table. Particularly suitable metals include aluminum, zinc, magnesium, lithium, cadmium, calcium and the like.

Suitable organo metal compounds include metal alkyls, metal alkyl halides or metal alkoxides which can be employed herein include, alkyl and aromatic metal compounds such as, for example, diethyl aluminum chloride, ethyl aluminum dichloride, diethyl aluminum bromide, ethyl aluminum dibromide, diethyl aluminum fluoride, ethyl aluminum difluoride, diethyl zinc, ethyl zinc chloride, dimethyl magnesium, dibutyl magnesium, methyl magnesium chloride, butyl lithium, diethyl aluminum methoxide, diethyl aluminum ethoxide, ethyl aluminum diisopropoxide, ethyl aluminum dibutoxide, phenyl magnesium bromide, tolyl magnesium bromide, phenyl aluminum dichloride, mixtures thereof and the like.

The cuprous halide containing quantities of cupric halide is treated with a sufficient quantity of the above mentioned organo metal compounds or halides or alkoxides thereof to reduce the cupric ion to the cuprous ion at a temperature of from about 0° C to about 70° C preferably from about 20° C to about 40° C for a time sufficient to reduce the cupric ion to the cuprous ion usually from about 0 to about 48 hours and preferably from about 1 to about 12 hours while in the presence of a suitable liquid solvent such as a paraffin, olefin or aromatic hydrocarbon.

Suitable quantities of the organo metal compounds is that stoichiometric quantity which will reduce the cupric ion present to the cuprous ion up to a slight excess, e.g. from stoichiometric to about 2.5 times stoichiometric, preferably from stoichiometric to about 1.5 times stoichiometric. Relatively large excess quantities of the organo metal compound including halide and alkoxides thereof tend to reduce some CuCl to metalic copper. While this is undesirable it does not cause serious problems. However, such can be eliminated or reduced by neutralizing preferably prior to formation of the complexing agent, the residual organo metal compound, organo metal halides or organo metal alkoxides with a halogen halide such as hydrogen chloride, hydrogen bromide or the like.

Particularly suitable solvents include, for example, toluene, benzene, ethyl benzene, xylene, mixtures thereof and the like.

The method for reacting the above treated cuprous halide with an aluminum halide to form the cuprous aluminum halide complexing or absorbing agent is well known as disclosed in the U.S. patents mentioned on pages 1 and 2 and such are incorporated herein by reference.

In those instances wherein the metal halide formed from the organo metalic reducing agent is insoluble, the resultant complexing agent is filtered to remove the insoluble compounds prior to use.

The following examples are illustrative of the invention and therefore should not be construed as to limiting the scope thereof in any manner.

EXAMPLE 1

An 8% solution of the diethylaluminum chloride in toluene was prepared by dissolving the neat aluminum alkyl conmpound in dry toluene (<1 ppm $H_2O$) under dry laboratory conditions. About 22 g of this solution (2.92 × $10^{-2}$ equiv.) was added to 11 g of cuprous chloride which contained considerable cupric contamination (3.4 wt. %, 5.89 × $10^{-3}$ equiv. of cupric ion). Almost immediately finely divided copper metal was noted in the reaction mixture. Then 20 ml of toluene and 10 g aluminum chloride were added and $AlCuCl_4$·toluene complex was formed with stirring and gentle heating. The mixture was filtered through a fine porosity sintered-glass filter. The solution was virtually colorless, with only a faint yellow tinge. However, after a few hours additional copper was noted at the bottom of the container, indicating that an excess of the aluminum alkyl compound was present. Hydrolysis of the sample yielded essentially no aromatic tars, as indicated from the nearly colorless hue of the complex. Had aromatic tars been formed, the solution would have turned black.

EXAMPLE 2

A. Comparative (Insufficient Quantity of Metal Alkyl Chloride)

To 11 g of cuprous chloride (containing 3.4 wt. %, 5.89 × $10^{-3}$ equiv. of cupric ion) was added 20 ml of a 3% solution of ethylaluminum dichloride in toluene. Little reaction was noted initially, but overnight the light green color of the solid changed to yellow. 13 g of aluminum trichloride was added and the resultant $CuAlCl_4$·toluene solution was greenish black in color indicating that the complex was not free of aromatic tars which also indicated that all of the cupric ions had not been removed from the cuprous chloride.

B. Present Invention (Use of Sufficient Quantity of Metal Alkyl Halide

To 6.7 g of the same cuprous chloride ($3.59 \times 10^{-3}$ equiv. of cupric ion) was added 11.5 g of toluene containing 6.9% ($6.25 \times 10^{-3}$ equiv.) ethylaluminum dichloride. After 12–14 hours, the cuprous chloride was clearly white. Then 7 g of anhydrous aluminum chloride was added and a colorless $CuAlCl_4$.toluene complex solution resulted. Only a minor amount of copper metal was noted as a by-product of the preparation. This experiment showed that aromatic tars are not formed when a sufficient quantity of ethylaluminum dichloride is employed.

EXAMPLE 3

Ethylaluminum sesquichloride was prepared by mixing equimolar quantities of ethylaluminum dichloride and diethylaluminum chloride. To 11 g of cuprous chloride (containing $5.89 \times 10^{-3}$ equiv. of cupric ion) was added 12 g of toluene containing 7.7% ($1.12 \times 10^{-2}$ equiv.) ethylaluminum sesquichloride. After 4–5 hours, it appeared that all cupric impurities had been removed. Then, 11 g of anhydrous aluminum chloride and some additional toluene were added to the reaction flask. The resulting $CuAlCl_4$.toluene complex was slightly yellow in color. This showed that ethylaluminum sesquichloride was also successful in preventing tar formation caused by cupric impurities. However, copper metal was formed even after the complex had been filtered, indicating that the complex itself was being destroyed.

Therefore, for best results, the residual quantities of organo aluminum halide should be neutralized prior to formation of the $AlCuCl_4$.toluene complex with a hydrogen halide such as HCl so as to prevent further reduction of the cuprous chloride to metallic copper.

We claim:

1. In a process for preparing cuprous aluminum tetrahalide complexing agents by reacting a cuprous halide containing contaminating quantities of cupric halide with an aluminum trihalide, the improvement which comprises treating the contaminated cuprous halide, prior to reacting with the aluminum trihalide, with an organo metal compound selected from the group consisting of metal alkyls, metal alkyl halides or metal alkoxides, wherein said metal is selected from Groups IA, IIA, IIB, and IIIA of the Periodic Table, in a quantity sufficient to reduce the cupric ion to the cuprous ion at a temperature of from about 0° C to about 70° C for a period of time sufficient to reduce the cupric ion to the cuprous ion.

2. The process of claim 1 wherein the quantity of organo metal compound is from stoichiometric to about 2.5 times the stoichiometric quantity required to reduce the cupric ion to the cuprous ion and the temperature is from about 20° C to about 40° C.

3. The process of claim 2 wherein the organo metal compound is employed in a quantity of from stoichiometric to about 1.5 times stoicnhiometric.

4. The process of claim 3 wherein the metal of the organo metal halide is selected from the group consisting of aluminum magnesium, calcium, zinc and cadmium.

5. The process of claim 4 wherein the metal of the organo metal compound is aluminum.

6. The process of claim 5 wherein the organo aluminum compound is selected from diethyl aluminum chloride, ethyl aluminum dichloride and ethyl aluminum sesquichloride.

7. The process of claim 6 wherein the solvent is toluene.

* * * * *